(12) United States Patent
Kovacich et al.

(10) Patent No.: US 8,847,579 B2
(45) Date of Patent: Sep. 30, 2014

(54) COMPACT PARAMAGNETIC OXYGEN SENSOR

(75) Inventors: Richard P. Kovacich, Crowborough (GB); Colin G. Stocks, Crowborough (GB); Christopher R. Edwards, Crowborough (GB); James D. Hobby, Crowborough (GB)

(73) Assignee: Servomex Group Limited (GB)

( * ) Notice: Subject to any disclaimer, the term of this patent is extended or adjusted under 35 U.S.C. 154(b) by 623 days.

(21) Appl. No.: 13/129,934

(22) PCT Filed: May 27, 2009

(86) PCT No.: PCT/GB2009/002702
§ 371 (c)(1),
(2), (4) Date: Aug. 18, 2011

(87) PCT Pub. No.: WO2010/058168
PCT Pub. Date: May 27, 2010

(65) Prior Publication Data
US 2011/0304322 A1    Dec. 15, 2011

(30) Foreign Application Priority Data
Nov. 19, 2008 (GB) .................................. 0821181.5

(51) Int. Cl.
*G01N 27/76* (2006.01)
*G01N 33/00* (2006.01)

(52) U.S. Cl.
CPC ............ *G01N 27/76* (2013.01); *G01N 33/0036* (2013.01)
USPC ............................ 324/201; 324/204; 73/25.02

(58) Field of Classification Search
None
See application file for complete search history.

(56) References Cited

U.S. PATENT DOCUMENTS

| 2,416,344 A | 2/1947 | Pauling |
| 2,744,234 A | 5/1956 | Walter |

(Continued)

FOREIGN PATENT DOCUMENTS

| CN | 2781366 Y | 5/2006 |
| CN | 102224416 A | 10/2011 |

(Continued)

OTHER PUBLICATIONS

GB Search Report dated Mar. 10, 2009, for GB 0821181.5 filed on Nov. 18, 2008; 3 pages.

(Continued)

*Primary Examiner* — Melissa Koval
*Assistant Examiner* — Stephen G Armstrong
(74) *Attorney, Agent, or Firm* — Daly, Crowley, Mofford & Durkee, LLP

(57) ABSTRACT

An apparatus for the measurement of the magnetic susceptibility of a gas mixture comprises: a gas sample chamber (8) adapted to receive the gas mixture; a test body (1) rotatably suspended within the gas sample chamber; magnets (10) within the gas sample chamber; a compact optical system for detecting rotation of the test body (1) including a light source (12), photodetectors (13) arranged to detect a light signal, and a mirror (5) attached to the test body (1). An actuation system is arranged to keep the test body (1) substantially at a null position. The optical system comprises at least one photodetector positioned on each side of the light source. The light source is arranged to emit a light beam towards the test body. The photo detectors are arranged to each detect an edge of a light beam reflected from the mirror.

17 Claims, 3 Drawing Sheets

(56) References Cited

U.S. PATENT DOCUMENTS

Figure 1:
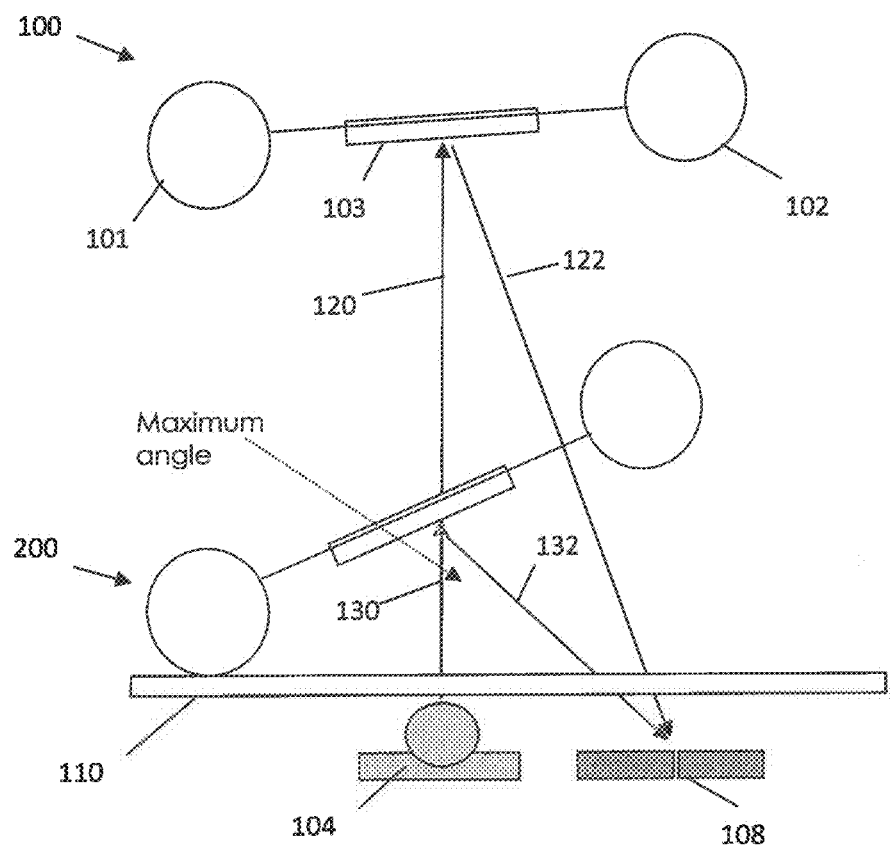

| | | | |
|---|---|---|---|
| 3,026,472 | A | 3/1962 | Greene et al. |
| 3,612,991 | A | 10/1971 | Greene |
| 3,826,947 | A | 7/1974 | Bowes et al. |
| 3,994,588 | A * | 11/1976 | Marx .................. 356/152.2 |
| 4,425,043 | A * | 1/1984 | van Rosmalen ......... 356/614 |
| 4,794,334 | A | 12/1988 | Kocache et al. |
| 4,983,913 | A | 1/1991 | Krause et al. |
| 4,988,946 | A | 1/1991 | Kocache et al. |
| 6,246,227 | B1 | 6/2001 | Hobby et al. |
| 7,102,346 | B2 | 9/2006 | Hobby et al. |
| 2009/0151424 | A1 * | 6/2009 | Huang et al. .............. 73/23.2 |

FOREIGN PATENT DOCUMENTS

| | | |
|---|---|---|
| DE | 10 2006 021 308 A1 | 10/2007 |
| GB | 746778 | 3/1956 |
| GB | 1 500 412 | 2/1978 |
| GB | 2 196 127 | 4/1988 |
| GB | 2465565 A | 5/2010 |
| WO | WO 2008/154981 A1 | 12/2008 |
| WO | WO 2010/058168 A1 | 5/2010 |

OTHER PUBLICATIONS

PCT Search Report and Written Opinion of the ISA dated Mar. 3, 2010, for PCT/GB/2009/002702 filed on Nov. 19, 20091 14 pages.
PCT International Preliminary Report on Patentability and Written Opinion of the ISA for PCT Pat. App. No. PCT/GB2009/002702; dated Jun. 3, 2011; 10 pages.
Kovacich et al.; "Highly Accurate Measurement of Oxygen Using a Paramagnetic Gas Sensor;" Institute of Physics Publishing; Measurement Science and Technology; vol. 17, No. 6; 2006; pp. 1579-1585.
Great Britain Notice of Allowance; dated Jul. 9, 2013; for GB Pat. App. No, 0821181,5; 2 pages.
Chinese First Office Action (English translation); dated May 24, 2013; for CN Pat. App. No. 200980146271.5; 5 pages.
Chinese First Office Action; dated May 24, 2013; for CN Pat. App. No. 200980146271.5; 7 pages.
Response filed Jan. 30, 2012; to European Official Communication; dated Jul. 20, 2011; for EP Pat. App. No. 09899127.7; 15 pages.
United Kingdom Examination Report; dated Sep. 17, 2012; for GB 0821181.5; 2 pages.
Response filed Jan. 18, 2013; to United Kingdom Examination Report; dated Sep. 17, 2012; for GB 0821181.5; 2 pages.
United Kingdom Examination Report; dated Feb. 6 2013; for GB 0821181.5; 3 pages.
Response filed Apr. 23, 2013; to United Kingdom Examination Report; dated Feb. 6, 2013; for GB 0821181.5; 9 pages.
United Kingdom Examination Report; dated May 14, 20131 for GB 0821181.5; 2 pages.
Response filed Jun. 21, 2013; to United Kingdom Examination Report; dated May 14, 2013; for GB 0821181.5; 4 pages.
Havens; "The Magnetic Susceptibility of Nitrogen Dioxide;" Physical Review, vol. 41; Aug. 1, 1932; pp. 337-344.
Chinese Office Action dated Feb. 18, 2014, for Chinese Pat. App. No. 200980146271.5; 3 pages.
Chinese Office Action dated Feb. 18, 2014, English translation; for Chinese Pat. App. No. 200980146271.5; 3 pages.
Chinese Office Action dated Feb. 18, 2014, English translation of Claim Rejections; for Chinese Pat. App. No. 200980146271.5; 2 pages.
Response dated May 5, 2014, to Chinese Office Action dated Feb. 18, 2014, Amended Claims; for Chinese Pat. App. No. 200980146271.5; 2 pages.
"Pm116 Fast Oxygen Transducer Instruction Manual," Servomex Group Ltd, Jan. 1, 2001; 39 pages.
Letter to China Science Patent and Trademark Agent Ltd. dated May 1, 2014; for Chinese Pat. App. No. 200980146271.5; 2 pages.

* cited by examiner

COMPACT PARAMAGNETIC OXYGEN SENSOR

CROSS REFERENCE TO RELATED APPLICATION

This application claims the benefit of International Patent Application PCT/GB2009/002702, filed Nov. 19, 2009, and published in the English language as WO2010/058168 A1, which application claims priority from GB Patent Application number GB0821181.5, filed Nov. 19, 2008.

FIELD OF INVENTION

This present invention relates to apparatus for the measurement of the amount of oxygen in a gas mixture, or other gas with significantly different magnetic susceptibility than the background gas mixture, by the use of a suspended test body in a magnetic field that experiences force due to the magnetic susceptibility of the measurand gas. So that the apparatus can be made compact, the optical system used to detect movement of the test body is specially arranged to reduce its size.

DESCRIPTION OF PRIOR ART

The measurement of oxygen gas by its paramagnetic property is a well established technique which is approved for many industrial and medical applications, where it generally provides excellent selectivity, accuracy and reliability. This is because oxygen is one of the few gases which exhibit paramagnetism, meaning it will be strongly attracted by a magnetic field. Most other common gases are diamagnetic, which is a very much weaker magnetic effect.

The force Fm that acts on a spherical test body in an inhomogeneous magnetic field is proportional to its volume V, the magnetic field gradient HdH/dz and the volume magnetic susceptibility difference between the test body X1 and surrounding sample gas X2 (see "The magnetic susceptibility of nitrogen dioxide", G G Havens, Phys. Rev. vol 41 (1932) pp. 337-344). That is:

$$Fm \propto V^* H^* dH/dz^* (X1-X2)$$

Since the volume magnetic susceptibility of the sample gas is proportional to the sample gas density, the force is proportional to the partial pressure of oxygen. The volume magnetic susceptibility of oxygen at room temperature is $1.9 \times 10^{-6}$ SI units, whereas nitrogen (a typical background gas) is $-6.7 \times 10^{-9}$ SI units. Therefore the force due to oxygen in the gas mixture, even small amounts, is substantially larger than other gas components, hence the excellent selectivity of this measurement principle to oxygen.

The force itself is quite weak, typically a few micro-newtons with pure oxygen for magnetic field strengths and test body volumes that can be practically achieved. Consequently a very sensitive system is required to measure this force with the necessary resolution required for oxygen sensing applications.

The typically preferred arrangement uses a magnetic susceptibility torsion balance inside a sealed cell which is arranged to admit the sample gas. The torsion balance comprises a test body having a particular shape, and filled with a diamagnetic gas such as nitrogen. The body is suspended in a non-uniform magnetic field in the sealed cell, and is typically balanced by initially filling the cell with nitrogen. When the cell is subsequently filled with a test gas containing oxygen, the paramagnetic oxygen gas is attracted to the stronger part of the magnetic field, and the test body rotates. This rotation is detected and used to indicate the oxygen content of the sample gas.

Such a device was first described by Havens (see reference above) who carefully studied the factors that govern sensitivity of the test body, in particular its shape, finding that a sphere is optimum. Other magnetic susceptibility torsion balances using different test bodies are known, and as early as 1850 (Faraday M (1851), Proc. R. Inst., vol. 1, p. 229). However, they did not match the sensitivity achieved by Havens.

The first commercial oxygen analyser using a magnetic susceptibility torsion balance was developed by Pauling, Wood and Sturdivant under US government contract NDCrc-38 (J. Am. Chem. Soc. 68 (1946), 795) and is disclosed in U.S. Pat. No. 2,416,344 (application filed 23 Aug. 1941). The test body consists of a pair of identical hollow glass spheres on either end of a rigid bar that is suspended by a fine glass fibre under tension, which provides a very soft torsion spring constant. The spheres are made as light as possible so the inertia is not much larger than the magnetic force, and balancing weights are also added to minimise the effect of orientation sensitivity. This assembly is placed between magnet poles that generate a strong magnetic field gradient and arranged so the force acting on both spheres reinforces the torque.

Movement of the test body is detected using an optical lever. This consists of a light source that makes a beam of light which reflects off a mirror at the centre of the test body and then onto an optical readout, which indicates displacement of the subtended beam. The beam displacement at the optical readout is proportional to the angular movement of the test body and the length of the optical lever arm, i.e. the distance between the mirror and the readout. Therefore good angular resolution may be obtained by increasing the optical lever arm length as necessary while maintaining focus of the beam spot on the readout.

The optical lever is also advantageous for rejecting errors due to rectilinear motion and vibration, as the angular movement is detected from the centre of a balanced test body that is only allowed to rotate about its principal axis.

Later inventions made significant improvements to its manufacturability and performance, in particular through the use of an electronic optical lever to detect and control motion of the test body using a feedback system. Munday in GB 746,778 discloses an optical lever feedback system in which a photoelectric cell is used as the optical readout and a wire coil, attached around the test body that conducts via the suspending wire, is used to provide feedback. The system keeps the test body at a null position by reacting to motion of the test body. By maintaining the test body substantially in the same position in this way, all measurements can be recorded at the position of maximum sensitivity. This is achieved by amplifying the photoelectric cell signal to generate a current in the wire coil that produces a magnetic torque equal and opposite to the perturbing force that would otherwise push the test body away from its null position, i.e. the magnetic force due to a change of the amount of oxygen in the sample gas. This current can then be measured in order to determine the magnetic force, and hence the oxygen content of the sample gas. A similar system is disclosed by U.S. Pat. No. 3,026,472, but feedback is provided by electrostatic actuation of the test body.

Modern oxygen sensors still use the optical lever with refinements (see "Highly accurate measurement of oxygen using a paramagnetic gas sensor", R P Kovacich, N A Martin, M G Clift, C Stocks, I Gaskin, J Hobby, Measurement Science and Technology, vol 17 (2006), pp. 1579-1585): a solid state source (light emitting diode) in place of an incandescent one and a pair of photodiodes connected in reverse polarity to provide a zero voltage null position when both photodiodes are equally illuminated, i.e. when the beam spot centre is exactly in between the photodiodes. Using a pair of photodiodes also has the advantage of rejecting common mode errors, such as intensity fluctuations of the light source.

This electronic optical lever feedback system gives much improved sensitivity, linearity and stability. However, the size of the optical lever is significant and for applications that require a compact oxygen sensor (e.g. having a volume less than 30 mm$^3$) such as for integrated medical systems, the traditional optical lever becomes difficult to implement. This is because the size and arrangement of standard optoelectronic components limit the minimum optical lever arm length. Even one of the most compact present-day implementations, namely the applicant's product, Servomex Pm1116, has an optical lever arm length of 20 mm plus additional space for the optoelectronic components.

Several inventions have tried using arrangements without the optical lever, such as an electrostatic sensing and actuation system as disclosed in U.S. Pat. No. 3,612,991 and an oscillating magneto-dynamic system as disclosed in U.S. Pat. No. 6,246,227. However, both have disadvantages: The electrostatic system requires gold plating of the test body which makes manufacture difficult, requires high voltages (up to 100 Volts) thus limiting compact electronic design, and is not as corrosion resistant as other metals such as platinum. Other plating metals are not suitable as they tend to be paramagnetic or more prone to corrosion. The oscillating system is disadvantaged by cross sensitivity to gases with a significantly different viscosity to molecular weight ratio, such as helium and halocarbons with heavy molecular weight; gases which are used as anaesthetic agents.

It is therefore desirable to provide an apparatus in which the optical lever arm length can be reduced, while still providing a high sensitivity to the oxygen content of the sample gas.

SUMMARY OF INVENTION

The present invention provides a compact apparatus for the measurement of the magnetic susceptibility of a gas mixture.

The apparatus comprises a gas sample chamber adapted to receive the gas mixture, and a test body rotatably suspended within the gas sample chamber about an axis of rotation and substantially symmetrical about a plane containing the axis of rotation; means for creating an inhomogeneous magnetic field within the gas sample chamber; means for detecting rotational motion of the test body, comprising a compact optical system including a light source and photodetectors arranged to detect a light signal indicative of the rotational motion; and an actuation system arranged to keep the test body substantially at a null position determined by said optical system, wherein the light source is positioned in the plane of symmetry, and at least one photodetector is positioned on each side of the plane of symmetry. The positioning of the light source and photodetectors allows a much more compact optical lever to be attained, compared with a standard geometry.

In order to improve performance, the apparatus further comprises an optical element positioned in front of the light source and/or photodetectors to modify properties of the light emitted by the light source or received by the photodetectors.

In order to achieve a compact and cost effective design, by comparison with conventional designs, it is preferable to mount the optoelectronic components (i.e. the preferred LED light source and the photodetectors) in the same plane, for example on a printed circuit board, and make the optical lever not much larger than the test body. This is in contrast with conventional designs, in which it is common practice to mount the light source and detectors separately and in different planes, according to the reflection angle. In order to obtain a strong optical lever signal the beam divergence of the light source should be as small as possible, so the reflected beam spot falls entirely on the photodetectors.

If the optical lever size is reduced (by bringing the test body closer to the light source) while the source and detectors are kept in the same plane, then in a typical arrangement the mirror must make a larger angle to compensate. However, the maximum angle is limited by the test body size and its distance to the window that separates the optoelectronics from the sample gas. This is illustrated in FIG. 1.

FIG. 1 shows schematically a test body 100 positioned in relation to a light source 104 and detectors 108. The test body 100 is formed in a dumbbell shape with nitrogen-containing glass spheres 101, 102 at either end, and a centrally mounted mirror 103. The test body is able to rotate about its centre, due to the paramagnetic force caused by a surrounding magnetic field (as described above), depending on the composition of the sample gas surrounding the test body. As indicated by the arrows 120, 122, the light from the light source 104 is reflected from the mirror 103 and directed onto the detectors 108, through a window 110 positioned between the sample gas chamber in which the test body is located, and the light source and detectors. In the null position, the centre of the light beam is directed onto the detectors when the test body 100 is, as illustrated, at only a very slight angle from parallel to the plane in which the light source and detectors are mounted, due to the relatively long distance between the source and the test body, i.e. the large optical lever size.

If the test body is instead positioned significantly closer to the source and detectors, as illustrated by the alternatively positioned test body 200 in FIG. 1, it can be seen that a much larger angle of the test body is required in order for the mirror to reflect the centre of the light beam from the light source onto the detectors, as indicated by the arrows 130, 132.

As shown by the position of the test body 200 in FIG. 1, by reducing the optical lever size, the maximum angle of rotation is reduced by the proximity of the test body to the window 110, and with the optical lever size reduced by the extent shown by position of the test body 200, the test body is in fact unable to rotate any further about its centre.

To overcome this limitation the present invention uses a different arrangement for the optical lever: The light source is placed in line with the plane of symmetry of the test body (e.g. in line with the mirror shown in FIG. 1), with a photodetector placed on either side of a plane which is normal (i.e. perpendicular) to the plane of symmetry and contains the rotation axis of the test body. The photodetectors may be a pair of photodiodes, connected electrically in reverse polarity so that a null signal is obtained upon equal illumination. Because of beam divergence from the light source, the light which is not reflected at normal incidence will be reflected at an angle that subtends towards a photodetector. Therefore the reflected beam pattern superimposed on the optical elements will show that the photodetectors sense using the edge of the beam spot rather than the centre as with a conventional optical lever. If the beam shape of the source is symmetric, equal illumination (i.e. the null position) occurs when the mirror is not angled and therefore the optical lever arm length can be much shorter. The light source and photodetector positions can also be separately displaced in a direction parallel to the test body rotation axis. However, the relative position of the optical components will affect the total amount of light received by the photodetectors and the differential signal they generate for the mirror rotation.

Although the concept of positioning photodetectors on either side of a light source is disclosed in various prior art patents, including U.S. Pat. No. 4,983,913 and UK patent 1,500,412, none of them teaches apparatus or techniques suitable for use in very compact sensors with very short optical path lengths. For example, they do not address the problems of near field optical detection that a compact design always encounters, in particular stray light from the partial reflection off the window that is always necessary to separate the optics from the sample gas chamber and irregularities in the reflected beam spot, which contributes significantly more error when the beam spot edges are being used for sensing.

Without addressing these problems, the false signals generated by these imperfections may lead to poor measurement stability. Furthermore, both of these documents disclose the positioning of the light source directly in front of the mirror, which arrangement does not lend itself to the most compact designs.

Therefore, in order to improve performance due to the above mentioned problems, in addition to optimisation of the type, size and position of the components used in the compact design as previously outlined, the invention may also include optical elements that allow better shaping of the beam, which has the advantage of reducing scattered light that may interfere with the optical lever signal. To concentrate the light onto the mirror, a focussing element such as a lens may be used, and this may be integrated into the source, e.g. by providing the light source as a light emitting diode (LED) with a built in lens cap. Apertures can also be used in front of the light source and photodetectors to spatially filter the beam, i.e. to spatially filter the portions of the beam that would contribute to stray light from partial reflections. However, more advanced optical elements, such as micro lens arrays, graded lenses or diffractive optical elements may be even more efficient. Such optical elements used to shape the beam may be integrated into a single device that fits in between the optical system and the window. Furthermore, by blocking the gap between the optical system and the window, the stray light from the window partial reflections are greatly suppressed. Although anti-reflection coatings could be used, this is not generally practical for reasons of chemical compatibility and cost.

If a monochromatic light source is used, such as a laser, then an optical element with diffractive or dispersive properties may be used to direct the beam in a way that varies with the angle of the mirror, which itself may be a diffractive or dispersive element. The wavelength of the source or properties of the diffractive or dispersive element may be adjusted to reflect the beam at any specified angle.

Embodiments of the invention will now be described, by way of example, with reference to the accompanying drawings, in which:

FIG. 1 illustrates schematically a conventional optical lever in a paramagnetic oxygen sensor, where size is limited by maximum angle of the test body;

FIG. 2(a) illustrates schematically an optical lever in a paramagnetic oxygen sensor of the present invention which overcomes the angle limitation, FIG. 2(b) illustrates in schematic plan view the reflected light beam superimposed on the detectors, and FIG. 2(c) illustrates a schematic plan view of the reflected light beam superimposed on the detectors when the light source and photodetectors are displaced parallel to the test body rotation axis, in accordance with a second embodiment;

FIG. 3(a) shows an exploded view of a measurement apparatus according to the invention, FIG. 3(b) shows a front view of the assembled apparatus, and FIG. 3(c) shows a front view of the test body mounted to the suspension plate.

DESCRIPTION OF PREFERRED EMBODIMENTS

Figure 2:
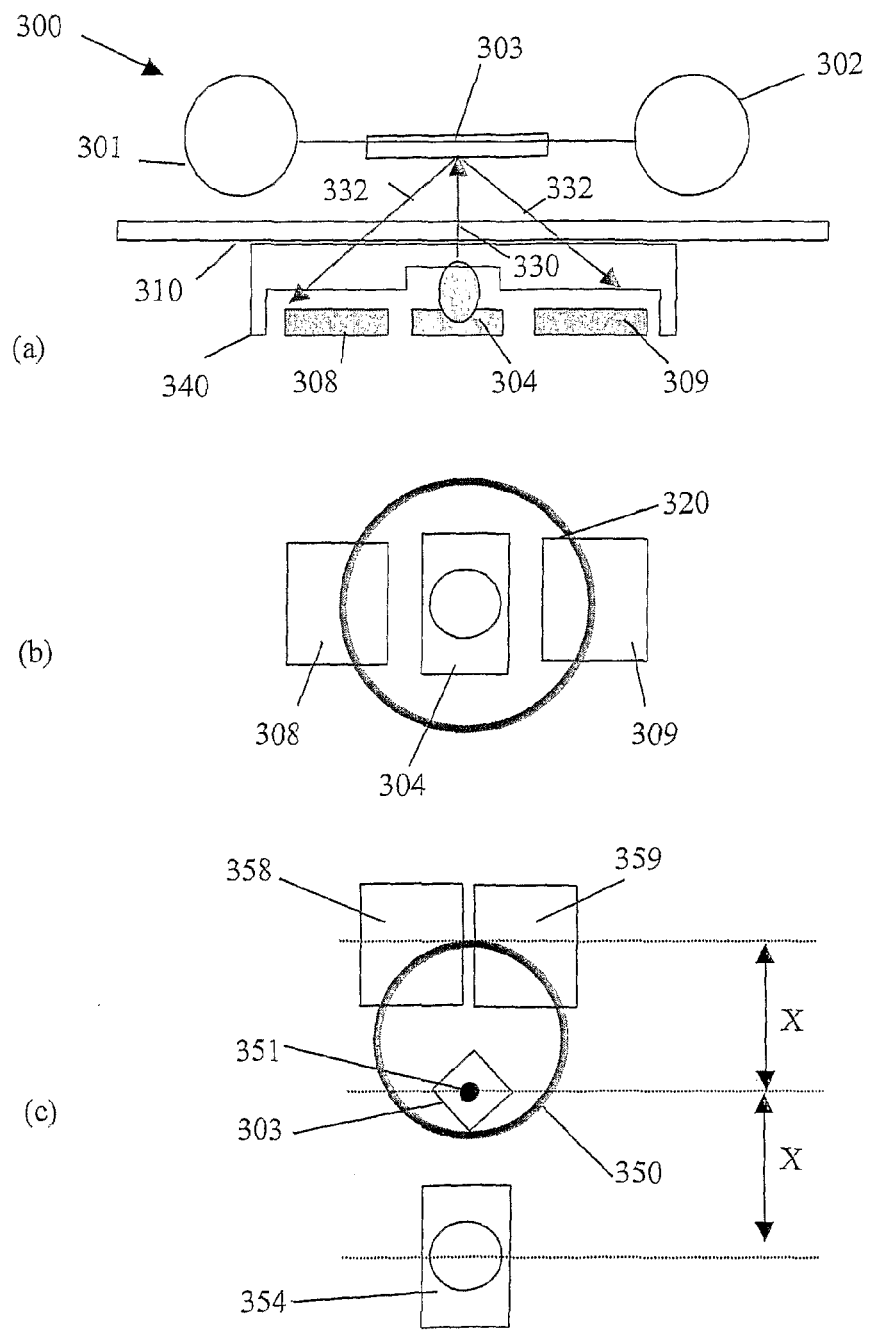

As discussed above, in accordance with the present invention, the photodetectors are placed on each side of the light source, and this arrangement is illustrated schematically in FIG. 2. That is to say, the light source is located in a plane normal to the mirror, where provided, or in a plane of symmetry of the test body, and through which the rotation axis of the test body passes, and the photodetectors are located such that at least one photodetector is positioned to one side of this plane, and at least one photodetector is positioned to the opposite side of this plane. FIG. 2(a) shows the test body 300, the same as that shown in FIG. 1, comprising glass spheres 301, 302 filled with nitrogen and mounted at either end of the test body, and having a mirror 303 mounted at its centre. The test body is positioned in the sample gas chamber (not shown), and is separated by a window 310 from a light source 304 and a pair of photodetectors 308, 309. The light source and photodetectors are mounted in the same plane as one another. However, in contrast with the arrangement shown in FIG. 1, the photodetectors 308, 309 are positioned symmetrically on either side of the light source 304, such that the null position of the test body 300 is a position in which the test body is parallel with the plane of the source and photodetectors (and in this case the window 310).

With regard to the spacing of the photodetectors from the light source, it can be seen that arrow 330 indicates the direction of the light beam from the light source towards the mirror 303. Since arrow 330 is directed normal to the mirror, and also towards the centre of the mirror, which corresponds substantially to the axis of rotation of the test body 300, arrow 330 effectively also illustrates an end view of the plane normal to the mirror and containing the rotation axis of the test body. It can therefore be seen from FIG. 2(a) that the light source is positioned in this plane, and that the photodetectors 380, 309 are spaced from the light source on opposite sides of this plane.

An optical element 340, which may be used to shape the beam and/or suppress stray light caused by partial reflections from the window 310, covers the light source 304 and photodetectors 308, 309. Where the optical element is designed to conform (i.e. re-shape) the beam, the optical element is arranged to increase the light reflected from the test body to the photodetectors, thereby increasing the optical lever signal and reducing the relative effect of any stray light. The optical element may incorporate multiple features to both spatially filter and conform the beam.

Although the centre of the light beam in this case is reflected back directly towards the source 304, and not onto the detectors as in the arrangement of FIG. 1, the rotation of the test body is still detected by virtue of the edge of the beam spot being reflected onto the detectors, due to divergence of the beam (see arrows 330, 332). This is shown in the plan view of FIG. 2(b), which illustrates the edge 320 of the beam from the light source 304 being reflected onto the detectors 308, 309.

As shown in FIG. 2(a), when compared with FIG. 1, by using this arrangement, the optical lever size can be greatly reduced, and the test body positioned much closer to the light source and detectors, while still allowing rotational movement of the test body.

The spacing between the photodetectors must be smaller than the beam spot size. However, there may be circumstances when the optical component packaging dimensions and tolerances do not allow this condition to be met properly. Therefore, in such circumstances it is beneficial to displace the light source and the photodetectors along a direction parallel to the test body rotation axis. Such an embodiment is shown by the schematic plan view in FIG. 2(c), where the light source 354 and photodetectors 358, 359 are both displaced by an equal amount X from a point below the mirror centre 351. It is now possible to bring the photodetectors very close together and thus use a smaller reflected beam spot as the optical lever generates a signal using a greater portion of the beam spot edge 350. In other words, by offsetting the light source and photodetectors from each other in a direction substantially parallel to the test body rotation axis, the light source can be moved from a position in which it is directly adjacent to, and between, the photodetectors, to a position which allows the at least two photodetectors to be located directly adjacent to one another. In particular, by displacing the light source and photodetectors in opposite directions by an equal amount X, as shown in FIG. 2(c), the most effective detection of the reflected light beam can be obtained while reducing the distance between the mirror and the plane of the light source and photodetectors.

Figure 3:
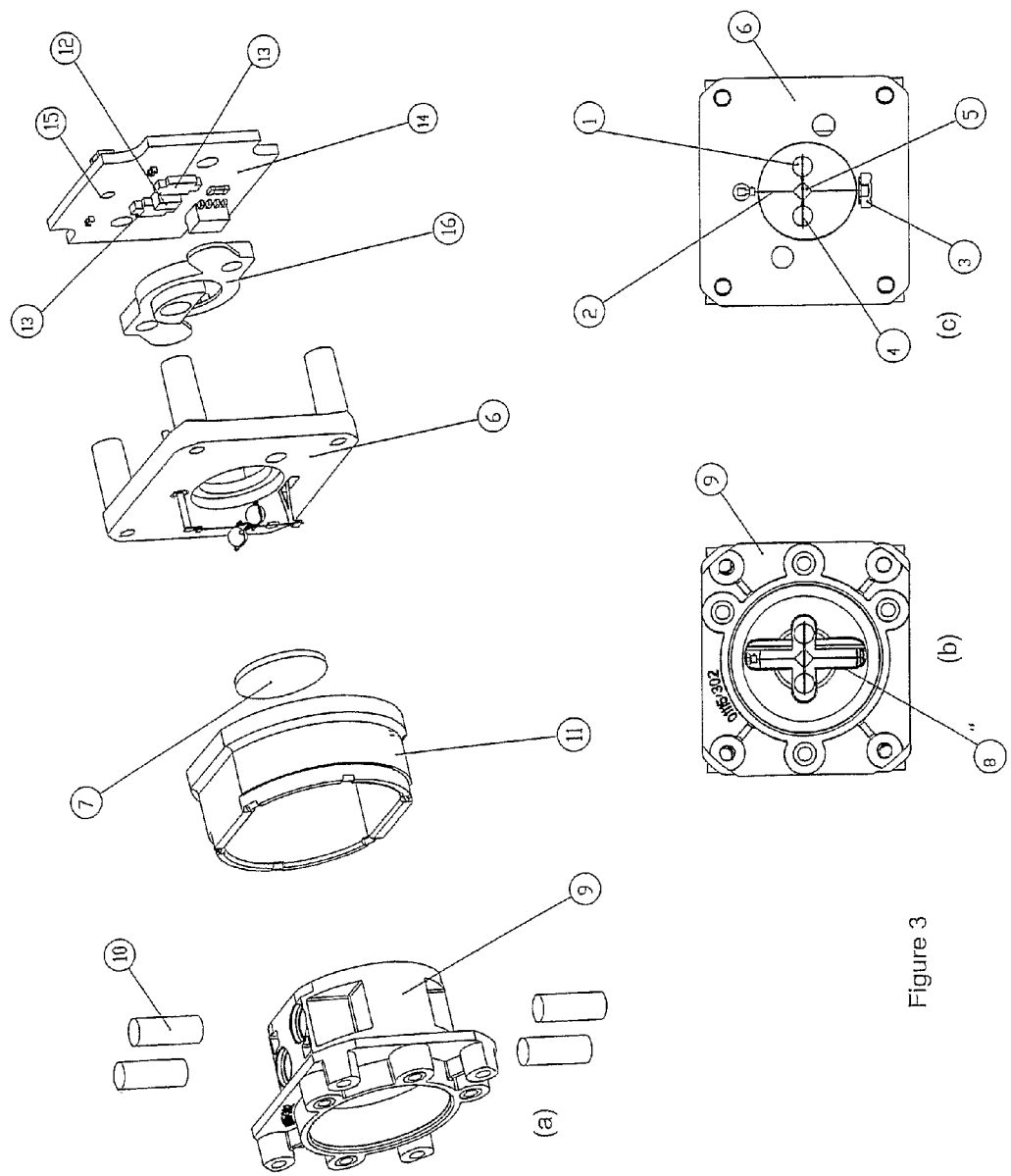

An embodiment of the present invention is shown in more detail in FIG. 3. The illustrated embodiment uses certain principles of operation which are generally known, and are outlined in previous patents, principally U.S. Pat. No. 4,988,946. As shown in FIG. 3(a), the test body 1, comprising borosilicate glass spheres filled with nitrogen, is suspended by a platinum-iridium alloy strip 2, which is welded onto spring posts 3 that maintain tension of the strip. The feedback coil 4, positioned around the test body spheres for magnetic actuation, is also made of platinum-iridium alloy and is sheathed in glass, as described in U.S. Pat. No. 3,826,974. This joins the suspension strip 2 to form an electric circuit. A platinum mirror 5 is positioned at the centre of the test body 1 and is also used as a base for welding the components of the test body.

The test body 1 is mounted on a suspension plate 6 so the mirror 5 faces towards a window 7 that seals the gas sample chamber 8. One spring post 3 is electrically insulated via a feed-through and the other post 3 is connected directly to the suspension plate 6. Once assembled, the window 7 is located in a corresponding recess in the suspension plate 6, between the test body 1 and the light source 12.

The suspension plate 6 fits into a non-magnetic piece 9 that holds a set of magnets 10 which generate the appropriate inhomogeneous magnetic field for the test body 1. The non-magnetic piece 9 is also shaped to form the gas sample chamber 8 within which the test body is rotatably mounted once the device is assembled, in such a way as to reduce the dead volume of the gas sample chamber 8, by being formed as two perpendicular channels in a cruciform configuration, respectively providing space for the test body 1 and the strip 2 on which it is mounted. (The provision of a cruciform chamber in which the test body is mounted is described in U.S. Pat. No. 4,988,946). A soft magnetic keeper 11, typically made of mild steel, surrounds the non-magnetic piece 9, which creates a magnetic circuit that concentrates all the magnetic flux at the test body. Fixing points on the magnetic keeper 11 allow a gas inlet header of choice to be mounted with any protective filter or mesh.

The optical lever consists of a surface mount light emitting diode (LED) 12, which preferably has an integral lens and two surface mount photodiodes 13, one on either side of the LED. In the illustrated embodiment, these components are mounted on a circuit board 14 that is fixed directly to the suspension plate 6 and facing the window. The spring post pin 3 that protrudes the suspension plate 6 contacts the circuit board 14 via a socket 15, while the other feedback coil 4 connection is through the circuit board 14 fixing.

The optical lever signal is processed by a conventional feedback loop circuit, which actuates the test body 1 to keep a null position that corresponds to equal illumination of the photodiodes 13. The feedback coil 4 current, which is proportional to the partial pressure of oxygen in the sample gas surrounding the test body 1, is monitored by a microprocessor circuit that calculates and reports the amount of oxygen present. The calibration data necessary for this calculation is stored by the microprocessor memory.

In a preferred embodiment, the microprocessor circuit is also operable to correct any temperature dependence by using temperature information, preferably provided by an on-board temperature sensor, and calibration data which may be factory calibration data. Alternatively or in addition, the apparatus may also include a pressure sensor to correct for pressure dependence.

If required to enhance performance, the invention may have an additional optical element 16 within the optical lever for better beam control. The optical element may be placed between the mirror 5 and LED 12, or take the place of the mirror 5 or window 7. The optical element may be: a lens; a lens array; a concave mirror; an aperture; a diffractive element; a dispersive element; a reflective element; or a birefringent element. As discussed above, such optical elements may be used in any appropriate configuration in the beam path between the light source and the photodetectors, to provide an effective detected signal at the photodetectors, which gives an accurate indication of the movement of the test body.

In particular, a diffractive element or lens array may be used in order to split the beam between the two photodetectors more effectively.

More detail regarding particular arrangements of optical elements is given below.

A lens is an example of an optical element designed to conform the beam so that more light is received by the photodetectors, in order to increase the optical lever signal. The use of a lens array considers the use of individual lenslets that are used to either focus the beam or, if they are sufficiently small, also to split the beam so that each part is directed towards one of the photodetectors via reflection off the mirror. The lenslets may also be used in front of the photodetectors to improve their light collection efficiency.

A diffractive element may be used when the source is highly monochromatic, i.e. a laser source, since the angle of diffraction can be used to direct light to the photodetectors, for example if the mirror is replaced by a diffractive surface. Furthermore, the symmetric property of diffraction can also be used to split the beam, thus, for example, achieving the ideal beam pattern shown in FIG. 2(a).

A birefringent element may be used when the source is polarized, since the difference between the ordinary and extra-ordinary beam propagation through a birefringent element may be used to split the beam.

A concave mirror may be used as an optical element in place of the mirror shown in FIG. 2(a), so that the reflected beam spot can be adjusted to any required size.

A dispersive element may be used when the source is polychromatic, since the dispersive property of the element can be used to split the beam, due to the beam having different wavelengths.

When the modification described above in the second embodiment is applied to the arrangement illustrated in FIG. 3, the light source 12 and photodetectors 13 are separately displaced along a direction parallel to the test body rotation axis, which is very closely approximated by the suspension strip 2. This allows closer spacing of the photodetectors, which allows a smaller beam spot size to be used.

The invention claimed is:

1. An apparatus for the measurement of the magnetic susceptibility of a gas mixture, comprising:
    a gas sample chamber (8) adapted to receive the gas mixture, and a test body (1) rotatably suspended within the gas sample chamber;
    magnets (10) for creating an inhomogeneous magnetic field within the gas sample chamber;
    a compact optical system for detecting rotational motion of the test body (1), the compact optical system including a light source (12), photodetectors (13) arranged to detect a light signal indicative of the rotational motion, and a mirror (5) attached to the test body (1) and arranged perpendicular to a main optical axis of the light source's emitted light beam; and
    an actuation system arranged to keep the test body (1) substantially at a null position determined by said optical system,
    wherein the optical system comprises at least one photodetector positioned on each of two opposing sides of the light source, wherein the light source is arranged to emit a light beam towards the test body, and the photodetectors are arranged to each detect an edge of a light beam reflected from the mirror.

2. The apparatus according to claim 1, further comprising at least one optical element positioned in front of the light source and/or the photodetectors to modify properties of the light emitted by the light source or received by the photodetectors.

3. The apparatus according to claim 2, wherein the at least one optical element comprises a focussing element arranged to increase the light signal received by the photodetectors.

4. The apparatus according to claim 2, further comprising a window positioned between the gas sample chamber and the optical system, wherein the at least one optical element is arranged to reduce stray light received by the photodetectors caused by partial reflections from the window.

5. The apparatus according to claim 2, wherein the at least one optical element is arranged to split a light beam emitted by the light source (12), whereby to direct the beam towards the photodetectors (13) positioned on either side of the light source.

6. The apparatus according to claim 2, wherein said at least one optical element is; an aperture; a lens; a lens array; a concave mirror; a diffractive optical element; a dispersive optical element; or a birefringent element.

7. The apparatus according to claim 6, wherein said at least one optical element is positioned at the rotational axis of the test body (1).

8. The apparatus according to claim 6, wherein said at least one optical element is positioned between the test body (1) and the light source (12).

9. The apparatus according to claim 1, wherein the light source and photodetectors are mounted on a common substrate.

10. The apparatus according to claim 9, wherein the substrate is a printed circuit board.

11. The apparatus according to claim 1, wherein the light source is a light emitting diode.

12. The apparatus according to claim 1, wherein the light source is a laser diode.

13. The apparatus according to claim 1, wherein the photodetectors are photodiodes.

14. The apparatus according to claim 1, wherein the test body (1) comprises a pair of hollow spheres positioned at either side of the rotational axis of the test body, and a mirror (5) located at the rotational axis, and wherein the test body is suspended in the gas sample chamber by a suspension strip (2).

15. The apparatus according to claim 14, wherein the actuation system comprises an electric feedback coil (4) positioned around the spheres of the test body, which forms a circuit through the suspension strip (2).

16. The apparatus according to claim 1, wherein the gas sample Chamber (8) is formed from a non-magnetic housing (9), and the test body (1) is mounted on a suspension plate (6), the apparatus being further ranged to position the housing (9) and the suspension plate (6) relative to one another such that the test body is positioned in the gas sample chamber.

17. The apparatus according to claim 16, wherein the housing (9) or the suspension plate (6) includes expansion ducts for facilitating the fast exchange of gas into the gas sample chamber (8), whilst minimising perturbation of the test body (1).

* * * * *